United States Patent [19]

Kim

[11] Patent Number: 5,321,162
[45] Date of Patent: Jun. 14, 1994

[54] HYPERBRANCHED ARAMIDS

[75] Inventor: Young H. Kim, Wilmington, Del.

[73] Assignee: E. I. Du Pont de Nemours and Company, Wilmington, Del.

[21] Appl. No.: 91,632

[22] Filed: Jul. 21, 1993

Related U.S. Application Data

[62] Division of Ser. No. 785,381, Oct. 30, 1991, Pat. No. 5,264,543.

[51] Int. Cl.$^5$ .............................................. C07C 331/00
[52] U.S. Cl. ..................................................... 560/317
[58] Field of Search ................. 560/317; 562/855, 868

[56] References Cited

U.S. PATENT DOCUMENTS 2,563,375 10/1949 Schenck ............................... 562/855
2,763,678 9/1956 Grimme et al. ...................... 560/317
4,857,630 8/1989 Kim ....................................... 528/397

FOREIGN PATENT DOCUMENTS

92/08749 5/1992 PCT Int'l Appl. .......... C08G 63/06

OTHER PUBLICATIONS

S. L. Kwolek et al., *Macromolecules*, 10:1390–1396 (1977).

*Primary Examiner*—José G. Dees
*Assistant Examiner*—Keith MacMillan

[57] ABSTRACT

Hyperbranched aramids, made from an aromatic aminodicarboxylic acid or an aromatic aminodicarboxylic acid, and optionally an aromatic aminocarboxylic acid are disclosed. The hyperbranched aramids are useful as aids for the processing of aramid solutions. Also disclosed are novel monomers used to make the hyperbranched aramids.

6 Claims, No Drawings

HYPERBRANCHED ARAMIDS

This is a divisional application of Ser. No. 07/785,381, filed on Oct. 30, 1991, now U.S. Pat. No. 5,264,543.

FIELD OF INVENTION

Hyperbranched aramids, made from aromatic diaminocarboxylic acid(s) or from aromatic aminodicarboxylic acid (s), are disclosed.

Also disclosed are monomers for making the hyperbranched aramids.

The hyperbranched aramids are useful as aids for processing aramid solutions.

TECHNICAL BACKGROUND

Hyperbranched polymers, sometimes also called dendrimers or starburst dendrimers are known, see for example a review article by D. A. Tomalia, et al., Angew. Chem. Int. Ed. Eng., vol. 29, p. 138-175 (1990), which is hereby included by reference. Most of these polymers are systematically built up, layer upon layer, by the controlled reaction of polyfunctional monomers, as described in Tomalia, et al. However, as also described on p. 153 of Tomalia, et al., there have been a few studies on such polymers where uncontrolled chain growth is carried out, usually in a single polymerization step. Polymers made in a single step are more conveniently made, but usually contain "defects", such as incomplete branching, when compared to polymers made by stepwise buildup of polymeric layers. None of the polymers described by Tomalia are aramids, that is contain amide groups in which both the nitrogen and carbonyl carbon atoms are bound directly to aromatic rings.

U.S. Pat. No. 4,857,630 describes the synthesis of hyperbranched polyarylenes by the uncontrolled polymerization of aromatic monomers of the $AB_2$ type. These reactions involved the formation of carbon-carbon bonds between benzene rings, and not the formation of amides.

C. J. Hawker, et al., J. Am. Chem. Soc., vol. 113, p. 4583-4588 (1991) describe the formation of "dendritic polyesters" by the uncontrolled self-condensation (polymerization) of 3,5-bis(trimethylsiloxy)benzoyl chloride to form a hyperbranched polyester. No mention is made of polymers containing amide groups.

K. E. Ulrich, et al., Polym. Mater. Sci., vol. 64, p. 237-238 (1991) report on an uncontrolled (one step) polymerization of 5-bromoresorcinol to form an aromatic polyether. No mention is made of amides.

N-Sulfinylaminobenzoyl chlorides are known, see for example S. L. Kwolek, et al., Macromolecules, vol. 10, p. 1390-1396 (1977). No mention is made of trifunctional compounds.

SUMMARY OF THE INVENTION

This invention concerns a hyperbranched aramid, consisting essentially of:

(a) about 10 to 100 mole percent of repeat units derived from one or more aromatic aminodicarboxylic acids, or one or more aromatic diaminocarboxylic acids; and (b) 0 to about 90 mole percent of repeat units derived from one or more aromatic aminocarboxylic acids; and provided that in said aromatic aminodicarboxylic acid said carboxyl groups are not ortho to one another, and that in said diaminocarboxylic acid said amino groups are not ortho to one another, and that in a biphenyl ring system carboxyl and/or amino groups are not in both a 2 and 2' position.

This invention also concerns a compound of the formula $ZA_2B$ wherein Z is benzenetriyl; and (a) A is N-sulfinylamino and B is halocarbonyl; or (b) A is halocarbonyl and B is N-sulfinylamino; and provided that both A groups are not ortho to one another.

DETAILS OF THE INVENTION

The polymers of the present invention are hyperbranched aramids. Such aramids are useful as processing aids for processing solutions of aramids, as in fiber spinning, as a solution rheology control agent, and as a multifunctional initiator (see for example U.S. Pat. No. 4,857,630). Aramids are polymers which contain amide linkages connecting aromatic rings, for example —ArNHC(O)Ar—. They are generally considered to be condensation polymers formally derived from aromatic amines and aromatic carboxylic acids, although the actual reactants that form the polymers may contain groups, other than amino or carboxylic acid, that react with each other to form the amide group connecting the aromatic rings.

By the term "aromatic aminodicarboxylic acid" herein is meant a compound that contains one amino group (or its equivalent) and two carboxylic groups (or their equivalents), each of these groups bound to a carbon atom of an aromatic ring. By the term "aromatic diaminocarboxylic acid" is meant a compound that contains two amino groups (or their equivalents) and one carboxylic group (or its equivalent), each of these groups bound to a carbon atom of an aromatic ring. The aromatic ring system in the aromatic aminodicarboxylic acid and the aromatic diaminocarboxylic acid is benzene or a biphenyl ring system. In the case of the aromatic aminodicarboxylic acid the carboxyl groups (or their equivalents) may not be ortho to each other. In the case of the aromatic diaminocarboxylic acid the amino groups (or their equivalents) may not be ortho to each other. If the aromatic group is a biphenyl ring system carboxyl and/or amino groups may not be in both a 2and a 2' position. By the term "aromatic aminocarboxylic acid" is meant a compound that contains one amino group (or its equivalent) and one carboxylic group (or its equivalent), each of these groups bound-to a carbon atom of an aromatic ring. Aromatic aminodicarboxylic acids, aromatic diaminocarboxylic acids and aromatic aminocarboxylic acids may contain inert groups, that is groups that do not react with the amino and carboxylic groups (or their equivalents). If the aromatic aminocarboxylic acid contains more than one aromatic ring, the amino group and the carboxyl group may be bound to any of the aromatic rings.

By a "biphenyl ring system" is meant any compound containing two benzene rings that are Joined by a covalent bond or are bonded together through a single atom, for example, as in diphenyl ether, diphenyl sulfone, and 2,2-diphenylpropane, as well as biphenyl itself.

It is preferred if the hyperbranched aramid contains less than 50 mole percent repeat units derived from an aromatic aminocarboxylic acid, more preferred if the aromatic aminocarboxylic repeat units are less than 20 mole percent of the aramid, and especially preferred if there are no aromatic aminocarboxylic derived repeat units in the aramid.

By an "equivalent" to an amino group is meant a group that reacts readily with a carboxylic acid (or its equivalent group) to form an amide. Conversely, by an "equivalent" to a carboxylic acid is meant a group that reacts readily with an amino group (or its equivalent group) to form an amide. Preferred amino equivalent groups are N-sulfinylamino, and amine hydrochloride, and a preferred carboxylic equivalent group is halocarbonyl [—C(O)X, where X is bromine or chlorine, especially chlorine].

It is preferred if the aromatic moiety in any of the monomer units is benzenetriyl. A preferred aromatic aminodicarboxylic acid is an aminobenzenedicarboxylic acid, especially 5-aminoisophthalic acid. A preferred diaminocarboxylic acid is a diaminobenzoic acid, especially 3,5-diaminobenzoic acid. A preferred aromatic aminocarboxylic acid is an aminobenzoic acid, especially 4-aminobenzoic acid.

It will be understood by skilled practitioners that all of the monomers used to make the hyperbranched aramids contain two types of reactive groups, an amino group or its equivalent and a carboxylic group or its equivalent, and these two groups are mutually reactive. Normally, one does not want reaction to occur until the proper mix of monomers is obtained under conditions which will yield high quality polymer. Thus it is desirable to somehow delay such reaction until polymer is to be made. Carboxylic groups and amino groups, although in principle reactive with each other, usually are not reactive enough in such polymerizations, so more reactive equivalents are used. Strategies have been developed to delay such reactions until desired.

S. L. Kwolek, et al., Macromolecules, vol. 10, p. 1390-1396 (1977), which is hereby included by reference, report two methods for making aramids from monomers that contain functional groups that are inherently reactive towards each other. In the first of these an N-sulfinylaminobenzoyl chloride is added to an amide solvent containing an equivalent of water. In this case, a poly(benzamide) is formed directly. In the second method, aminobenzoyl chloride hydrochloride is dissolved in an N,N-dialkylamide. The amino group is freed of the hydrochloride in these solvents, and polymerization proceeds. Both of these methods allow synthesis of a reactive precursor to a monomer that actually polymerizes, and then controlled polymerization. Analogs of these methods may be used to prepare the instant hyperbranched aramids, for instance, see Examples 5-7 and 9-11.

These hyperbranched polymers have a functional group present in them. If an aromatic diaminocarboxylic acid is used to make the hyperbranched aramid the polymer will contain amino groups (or their equivalents used in the polymerization). If an aromatic aminodicarboxylic acid is used to make the hyperbranched aramid the polymer will contain carboxyl groups (or their equivalents used in the polymerization). D. A. Tomalia, et al., supra, discusses the number of functional (branch ends) that can be expected in an "ideal" hyperbranched polymer. However, as pointed out by C. J. Hawker, et al., supra, uncontrolled polymerization to form hyperbranched (dendritic) polymers often leads to defects in the polymer structure.

The functional groups in the polymer may be further reacted with other compounds to graft different moieties onto the polymer. Alternatively the functional groups or groups derived from them may be used as initiation sites to graft different oligomeric or polymeric chains onto the hyperbranched aramid.

This invention also concerns a compound of the formula $ZA_2B$ herein Z is benzenetriyl, and either A is N-sulfinylamino and B is halocarbonyl or A is halocarbonyl and B is N-sulfinylamino. By "benzenetriyl" is meant a trivalent benzene radical, and the 1,3,5-benzenetriyl radical is preferred. By "halo" in halocarbonyl is meant chloro or bromo, and chloro is preferred. Preferred compounds of the type $ZA_2B$ are 1,3-bis (N-sulfinylamino)-5-halocarbonylbenzene and 1,3-bis (halocarbonyl)-5-N-sulfinylbenzene, and especially preferred compounds are 3,5-bis (N-sulfinyl-amino)benzoyl chloride and 5-N-sulfinylaminoisophthaloyl chloride. In all cases, the A groups, whether N-sulfinylamino or halocarbonyl, may not be ortho to each other.

Compounds of the type $ZA_2B$ can be made by reaction of the corresponding diaminobenzoic acid or aminobenzenedicarboxylic acid with at least 3 moles of $SOCl_2$, as generally described by S. L. Kwolek, et al., supra, from aminobenzoic acid, and in Examples 1 and 3, herein. The $ZA_2B$ compounds are useful as monomers, or intermediates for monomers, for making hyperbranched aramids, as described herein.

EXAMPLES

In the following Examples, these abbreviations are used:
DMAc—N,N-dimethylacetamide
DMF—N,N-dimethylformaide
GPC—gel permeation chromatography
Mn—number average molecular weight
NMP—N-methylpyrrolidone
TGA—thermogravimetric analysis
THF—tetrahydrofuran
PD—polydispersity, the weight average molecular weight divided by the number average molecular weight All of reactions were carried out under nitrogen atmosphere unless mentioned otherwise. The glassware was dried in an oven heated at 145° C.

EXAMPLE 1

Synthesis of 5-N-Sulfinyl Amino Isophthaloyl Chloride

To 36.23 g of 5-amino isophthalic acid was added 70 ml of thionyl chloride, and the mixture was refluxed for 16 hours, or until all of the solid dissolves in. Excess thionyl chloride was distilled off, then the resulting product was distilled at 135° C./0.6 mm Hg as clear slightly viscous yellow liquid. The yield was 31.38 g. $^1H$ NMR: 8.80 (2H), 8.81 (1H). $^{13}C$ NMR: 129.39 (C—H), 129.66 (CH), 135.32 (C—C), 142.62 (C—N), 166.61 (C=O).

EXAMPLE 2

Synthesis of 5-Amino Isophthaloyl Chloride Hydrogen Chloride 5.0 g of 5-N-sulfinyl amino isophthaloyl chloride (Example 1) was dissolved in 150 ml of ether, and anhydrous hydrogen chloride gas was bubbled through for 2 hours. Beige colored precipitate, which weighed 3.71 g after filtration, was obtained. This product was soluble in an amide solvent, such as N,N'-dimethyl acetamide or formamide. However, solution NMR of this product could not be obtained, since it polymerizes in those solvents. Elemental analysis calculated as $C_8H_6NO_2Cl_3$:

Theory: C: 37.76, H: 2.38 N: 5.50. Found C:40.98 H:2.74, N: 6.33.

EXAMPLE 3

Synthesis of 3,5-bis(N-Sulfinylamino)Benzoyl Chloride

To 42.14 g of 3,5-diamino benzoic acid was added 121 ml of of thionyl chloride and refluxed for 4 hr. Excess thionyl chloride was distilled off, and then the 3,5-bis(-sulfinylamino)benzoyl chloride was distilled under vacuum (140°–142° C./0.22 nun Hg) to give 17.15 g of the product, which solidified at room temperature. $^1$H NMR 8.51 (2H), 8.57 (1H).

EXAMPLE 4

Synthesis of 3,5-diaminobenzoyl Chloride Hydrogen Chloride 5.0 g of, 5-bis(sulfinylamino)benzoyl chloride was dissolved in 125 ml of diethyl ether and and anhydrous hydrogen chloride gas was bubbled through for 2 hours. Beige colored precipitate, which weighed 3.92 g after filtration, was obtained. This product was soluble in an amide solvent, such as DMAc or DMF. However, solution NMR of this product could not be obtained, since it would polymerized in those solvents. Elemental analysis calculated as $C_7H_9N_2OCl_3$: Theory C: 34.53, H: 3.73 N: 11.50. Found: C:34.44, H:2.78, N: 11.63.

EXAMPLE 5

Synthesis of Polymer from 5-aminoisophthaloyl Chloride Hydrogen Chloride

To a 500 ml resin kettle with a stainless egg beater type stirrer fitted with a nitrogen inlet and $CaSO_4$ tube outlet was added 200 ml of NMP and 15.6 g of $CaCl_2$. It was warmed with until all of the salt dissolved. The resin kettle was immersed in an ice bath, and was stirred for 30 min in the ice bath to ensure low temperature. To this was added 6.76 g of 5-aminoisophthaloyl chloride and then the ice bath was removed, and stirring was continued for 2 hrs. The solution was poured into water in a blender, and a white opaque precipitate was formed. The precipitate was collected by filtration after the solution was centrifuged at 13,000 rpm for 4 hours. After air drying 6.0 g of the product was obtained. NMR and TGA analysis indicated that NMP was still present. $^1$H NMR (d-DMF): 8.0, 8.5, 8.55, 8.65, 8.95, 11.1. $^{13}$C NMR (d-DMF): 122.8, 123.8, 124.3, 124.6, 125.0, 125.6, 125.7, 126.2, 132.8, 136.5, 136.7, 140.9, 166.2, 167.5. GPC molecular weight in DMAc/LiBr/$H_3PO_4$/THF: Mn=46,000, PD=2.53 (against polystyrene standard).

EXAMPLE 6

Synthesis of Polymer from 5-aminoisophthaloyl Chloride Hydrogen Chloride with a Base To a 500 ml resin kettle with a stainless egg beater type stirrer fitted with a nitrogen inlet and $CaSO_4$ tube outlet was added 200 ml of NMP and 15.6 g of $CaCl_2$. It was warmed until all of the salt dissolved in. The resin kettle was immersed in an ice bath, and was stirred for 30 min in the ice bath to ensure low temperature. To this was added 6.76 g of 5-amlnolsophthaloyl chloride hydrogen chloride and then the ice bath was removed, and stirring was continued for 4 hrs. To this was added 5.56 g of $Ca(OH)_2$ followed by 30 ml of methanol, and was stirred for another 30 min. The solution was poured into water in a blender, and a white opaque precipitate was formed. The precipitate was collected by filtration after the solution was centrifuged at 13,000 rpm for 4 hours. After air drying 6.70 g of the product was obtained. TGA analysis indicated that NMP was still present. Once dried, this polymer did not dissolve in either of NMP, DMAc, DMF.

EXAMPLE 7

Synthesis of Polymer from 5-aminoisophthaloyl Chloride Hydrogen Chloride

To 70 ml of NMP 0° C. was added 1.27 g of 5-aminoisophthaloyl chloride hydrogen chloride, and then it was stirred for 6 hr at room temperature. The solution was poured into water in a blender, and a white opaque precipitate was formed. The precipitate was collected by filtration after the solution was centrifuged at 13,000 rpm for 4 hours. After drying at 100° C. under vacuum, 1.25 g of the product was obtained. NMR and TGA analysis indicated that NMP was still present. The $^1$H NMR and $^{13}$C NMR spectra of this sample was exactly same as the polymer from Example 5. GPC molecular weight in DMAc/LiBr/$H_3PO_4$/THF: Mn=30,600, PD=3.24 (against polystyrene standard).

EXAMPLE 8

Synthesis of Methyl Ester of Polymer From 5-aminoisophthaloyl Chloride Hydrogen Chloride To 70 ml of NMP at 0° C. was added 1.27 g of 5-aminoisophthaloyl chloride hydrogen chloride, and then it was stirred for 6 hr at room temperature. Then 5 ml of methanol was added. The solution was poured into water in a blender, and a white fine precipitate was formed. The precipitate was collected by filtration after the solution was centrifuged at 13,000 rpm for 4 hours. After drying under vacuum, 1.07 g of amber brown product was obtained. NMR and TGA analysis indicated that DMP was still present. GPC molecular weight in DMAc/LiBr/$H_3PO_4$/THF: Mn=23,500, PD=2.43 (against polystyrene standard). The $^1$H NMR spectrum of this sample showed a broad peak at 3.9 ppm, due to the methyl ester group, in addition to the aromatic peaks, which are identical to the polymer in the Example 5.

EXAMPLE 9

Synthesis of Polymer from 5-sulfinylamino Isophthaloyl Chloride

To a clear burgundy solution of 26.41 g of 5-sulfinylamino isophthaloyl chloride in 200 ml of NMP was added 1.80 g of water in 30 ml of NMP from a dropping funnel over 13 minute period. The solution turned brown as water was added. After an additional 2 hours of mixing, the solution was poured into 300 ml of water to give gray colored precipitate. It was filtered and air dried. As it was dried it became dark brown, but when it was triturated with methanol it became gray again. Gray colored powder was filtered and dried in air to give 17.5 g of polymer.

EXAMPLE 10

Synthesis of Polymer from 3.5-diaminobenzoyl Chloride Dihydrogen Chloride

To a 500 ml resin kettle with a stainless egg beater type stirrer fitted with a nitrogen inlet and $CaSO_4$ tube outlet was added 200 ml of NMP and 2.87 g of $CaCl_2$. It was warmed with until all of the salt dissolved in. The resin kettle was immersed in an ice bath, and was stirred for 30 rain to ensure low temperature. To this was added 1.12 g of 3,5-diaminobenzoyl chloride dihydrogen chloride and then the ice bath was removed, and stirring was continued for 2 hrs. The solution remained clear orange and was poured into 500 ml water in a blender, but no precipitate formed. To this was added 100 g of ammonium sulfate and the clear solution was left for 16 hr. A fine pulp like mixture of the polymer and hexagonal needle type crystals of ammonium crystals (11.62 g) was obtained.

EXAMPLE 11

Synthesis of Polymer From 3,5-bis(sulfinylamino)-benzoyl Chloride Dihydrogen Chloride To a clear orange solution of 10.00 g of 3-sulfinyl amino isophthaloyl chloride in 300 ml of NMP was added 0.78 g of water in 30 ml of NMP from a dropping funnel, over a 13 minute period. The solution turned brown as water was added. After an additional 2 hours of mixing, the solution was poured into 300 ml of water, but no precipitate was formed until an excess of ammonium sulfate was added.

EXAMPLE 12

Liquid Crystalline Properties of Polymers

Polymers of Examples 5, 7, 8, 9 exhibit lyotropic properties under polarized light microscopy. Thus when the polymer of Example 8 was mixed with NMP under shear in a mortar, a viscous gel-like mixture was obtained. With 20 wt % polymer, it did not show birefregency at room temperature, but polymer solutions of concentrations higher than 40% exhibit a nematic phase of liquid crystalline texture under a polarized light microscope at room temperature.

| Polymer Concentration (wt %) | Birefrigency at Room Temperature | Clearing Temperature |
| --- | --- | --- |
| 20 | no | N/A |
| 40 | weak | ~60° C. |
| 55 | strong | >150° C. |
| 70 | strong | >150° C. |

A 50 wt % solution of the methyl ester of poly(5-aminoisophthaloyl chloride) of Example 8 also showed birefringency at room temperature, but it became isotropic at below 80° C. Lyotropic texture returned after about one day standing at room temperature.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A compound of the formula $ZA_2B$ wherein Z is benzenetriyl; and
   (a) A is N-sulfinylamino and B is halocarbonyl; or
   (b) A is halocarbonyl and B is N-sulfinylamino; and provided that both A groups are not ortho to one another.

2. The compound as recited in claim 1 wherein said Z is 1,3,5-benzenetriyl.

3. The compound as recited in claim 1 wherein said halocarbonyl is chlorocarbonyl.

4. The compound as recited in claim 2 wherein said halocarbonyl is chlorocarbonyl.

5. The compound as recited in claim 4 which is 3,5-bis(N-sulfinylamino)benzoyl chloride.

6. The compound as recited in claim 4 which is 5-N-sulfinylaminoisophthaloyl chloride.

* * * * *